United States Patent [19]

Ogawa

[11] Patent Number: 4,740,755
[45] Date of Patent: Apr. 26, 1988

[54] REMOTE CONDUCTIVITY SENSOR HAVING TRANSFORMER COUPLING IN FLUID FLOW PATH

[75] Inventor: Francis T. Ogawa, Lakewood, Colo.

[73] Assignee: Cobe Laboratories, Inc., Lakewood, Colo.

[21] Appl. No.: 869,132

[22] Filed: May 30, 1986

[51] Int. Cl.⁴ ............................................ G01N 27/07
[52] U.S. Cl. .................................... 324/445; 324/450; 324/442
[58] Field of Search ............... 324/439, 442, 445, 446, 324/450

[56] References Cited

U.S. PATENT DOCUMENTS

| | | | |
|---|---|---|---|
| 3,387,209 | 6/1968 | Eames et al. | 324/439 X |
| 3,396,331 | 8/1968 | Sperry, III | 324/445 |
| 3,404,336 | 10/1968 | Rosenthal | 324/445 |
| 3,980,946 | 9/1976 | Fleury | 324/445 |
| 4,138,639 | 2/1979 | Hutchins | 324/442 |

FOREIGN PATENT DOCUMENTS 831692 3/1960 United Kingdom ................ 324/445

OTHER PUBLICATIONS

Great Lakes Instruments, Inc., Models 32014 and 33324, Electrodeless Conductivity Sensors, Data Sheet 30002/1081.
Great Lakes Instruments, Inc., Electrodeless Conductivity Analyzers, Data Sheet S75A/1182.

*Primary Examiner*—Reinhard J. Eisenzopf
*Assistant Examiner*—Jack B. Harvey

[57] ABSTRACT

A cell for remotely sensing conductivity of a fluid passing through it, the cell having an inlet and an outlet and two fluid paths between the two, thereby defining a fluid loop, an excitation transformer comprising a first toroidal core having a hole through it and wire turns around it, the core encompassing a portion of the fluid loop therein, and a sensing transformer comprising a second toroidal core having a hole through it and wire turns around it, the core encompassing a portion of the fluid loop, the cores being coplanar to thereby reduce leakage between the transformers.

4 Claims, 2 Drawing Sheets

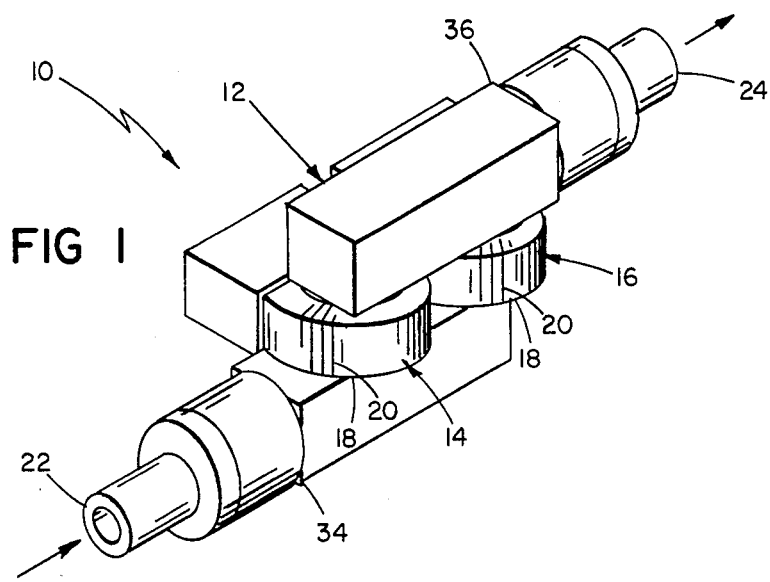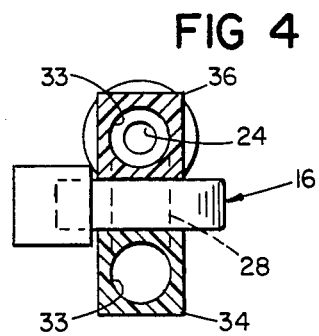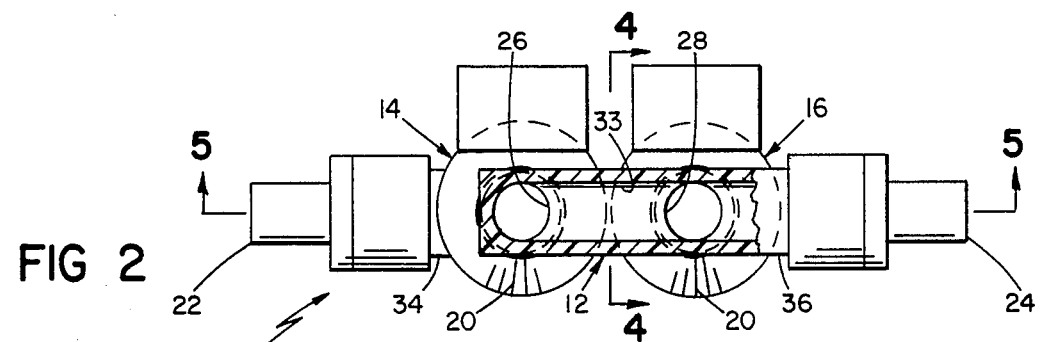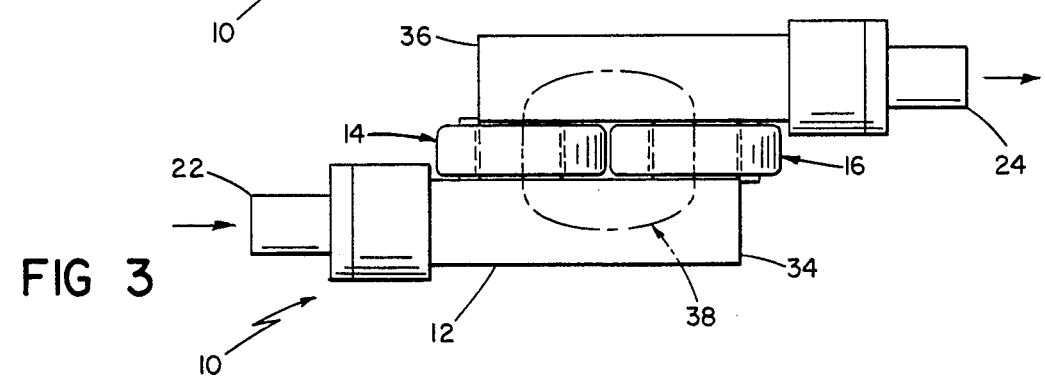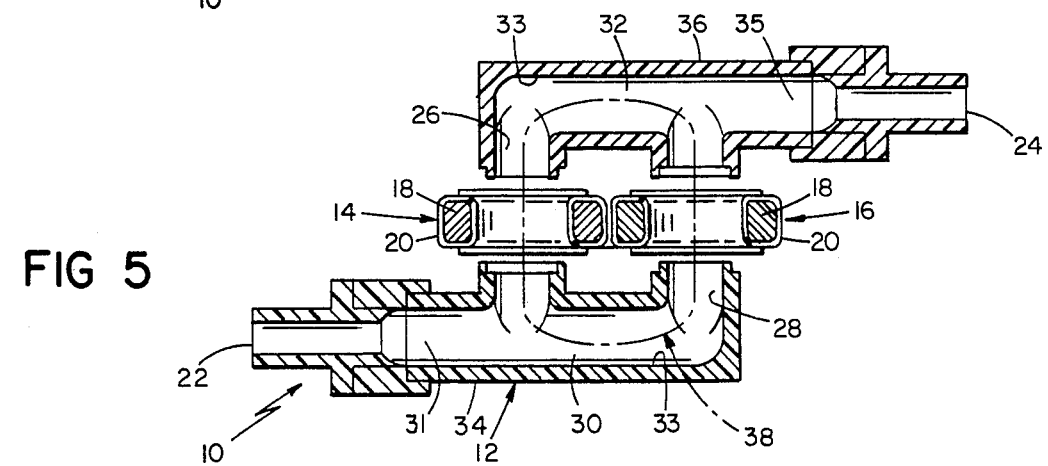

REMOTE CONDUCTIVITY SENSOR HAVING TRANSFORMER COUPLING IN FLUID FLOW PATH

FIELD OF THE INVENTION

The invention relates to remotely sensing conductivity of fluid flowing in a conduit, and in particular to sensing conductivity of dialysate in a dialysate preparation and supply machine.

BACKGROUND OF THE INVENTION

Conductivity of dialysate in a dialysate preparation and supply machine is typically measured by sensors that are immersed in the dialysate in a conduit and are subject to long term drift, owing to formation of film and precipitates on the electrodes, and to other shortcomings.

Electrodeless conductivity sensors, e.g., those available from Great Lakes Instruments, Inc., Milwaukee, Wis., have been used in water quality and process control. In one of these sensors, the conductivity of fluid flowing in a fluid flow conduit is remotely measured by providing a fluid loop connected to the conduit and two transformers coupled with the loop, inducing an electrical current in the fluid loop with one transformer, measuring the current induced in the other transformer by the current in the fluid loop, and determining the conductivity in the liquid using resistance, current and voltage relationships.

SUMMARY OF THE INVENTION

I have discovered that I could provide reduced leakage coupling between the excitation and sensing transformers of a two-transformer/fluid-loop remote conductivity sensor by using coplanar toroidal ferrite cores in excitation and sensing transformers.

In preferred embodiments a desirably low fluid loop length to fluid cross-sectional area ratio is provided by a fluid flow conduit having two circular portions that pass through the two toroidal magnets and are connected to each other by first and second connecting portions, the inner diameters of the toroidal magnets and wire turns around them being approximately equal to the outer diameters of the circular conduit portions, the connecting conduit portions being approximately equal in length to the diameters of the toroidal magnets and wire turns around them; the connecting portions extend in a straight line beyond the circular conduit portions to the inlet and the outlet to avoid corners at which bubbles could collect; and the connecting portions have opposing flat outer surfaces for holding the toroidal transformers in place.

Other advantages and features of the invention will be apparent from the following description of the preferred embodiment thereof and from the claims.

DESCRIPTION OF THE PREFERRED EMBODIMENT

The drawings will be described first.

Drawings

FIG. 1 is a perspective view of a conductivity cell according to the invention.

FIG. 2 is a plan view, partially in section, of the FIG. 1 cell.

FIG. 3 is an elevation of the FIG. 1 cell.

FIG. 4 is a vertical sectional view, taken at 4—4 of FIG. 2, of the FIG. 1 cell.

FIG. 5 is a diagrammatic exploded sectional view of the FIG. 1 cell.

STRUCTURE

Figure 6:
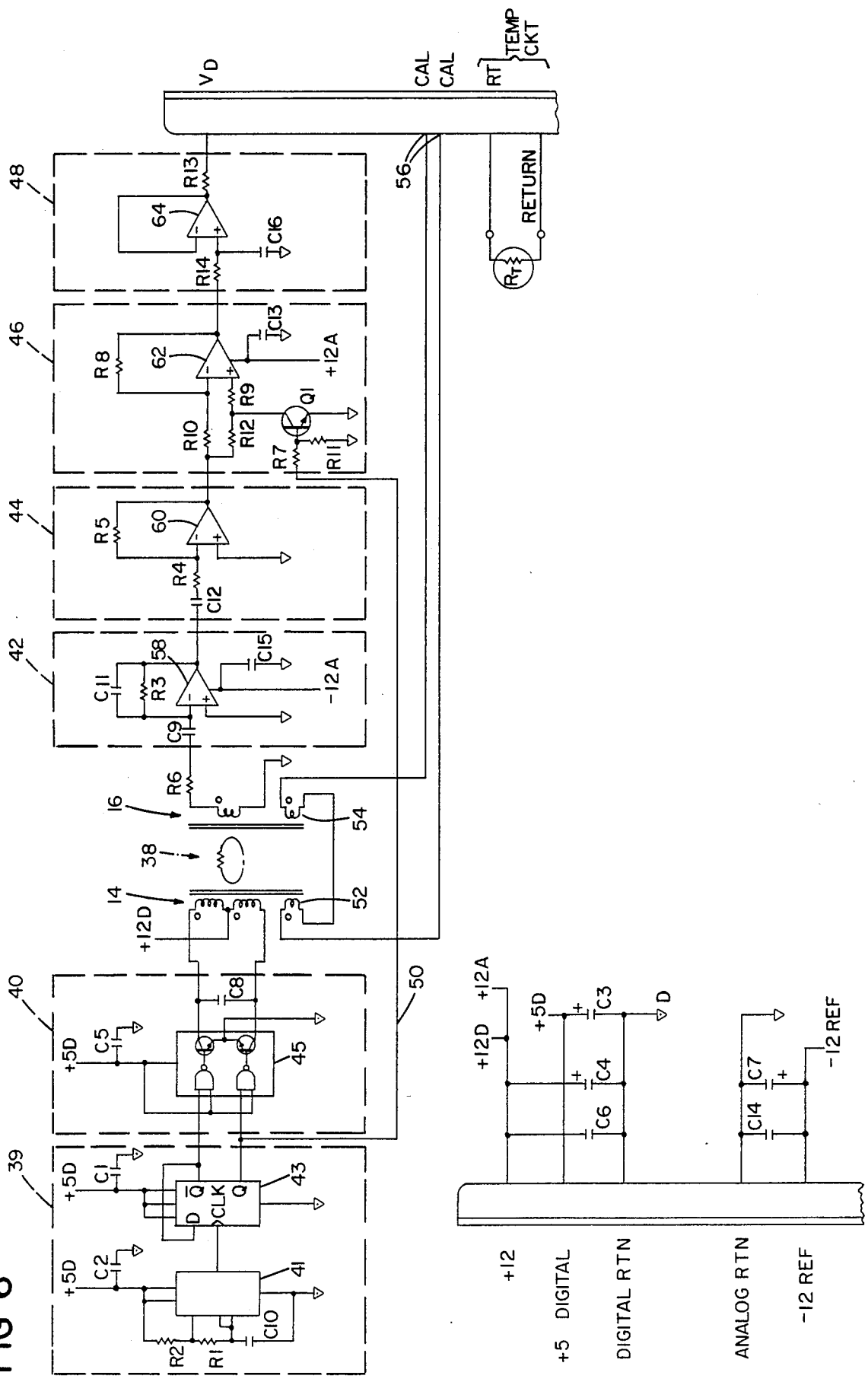
FIG. 6 is an electrical schematic of the electrical components of the excitation and sensing circuitry connected to the FIG. 1 cell.

Referring to FIGS. 1-5, there is shown conductivity cell 10, including plastic fluid flow conduit 12, excitation transformer 14 and sensing transformer 16. Excitation transformer 14 and sensing transformer 16 each include a toroidal core 18 and wires 20 wrapped around the core. Cell 10 is mounted in the dialysate flow path of a dialysate preparation and supply machine of the general type described in U.S. Pat. No. 4,371,385, which is hereby incorporated by reference, at a position along the dialysate supply conduit downstream of the mixing of concentrate with water and is connected to a processor to control the addition of concentrate to water.

Channel 12 has inlet 22, outlet 24, circular conduit portions 26, 28 (through transformers 14, 16) and connecting portions 30, 32 between them. In line with connecting portion 30 and extending beyond circular conduit portion 26 to inlet 22 is extension 31. In line with connecting portion 32 and extending beyond circular conduit portion 28 to outlet 24 is extension 35. Connecting portions 30, 32 have flat outer surfaces and circular inner surfaces 33 defining fluid flow channels therein (FIG. 4). As seen best in FIG. 4, the outer diameter of the circular conduit portion 26 is close in size to the inner diameter of toroidal core 18 and the wire turns on it, resulting in the largest practical cross-sectional area for the fluid flow path permitted by the dimensions of the cores. Also, the height of circular conduit portion is only slightly more than the thickness of toroidal core 18 and the wire turns on it, and there is a small distance between transformers 14, 16 (thus the length of the connecting portions between circular conduit portions is only slightly more than the diameter of the toroidal cores and the wire turns on them). These two factors provide a low value for the ratio of the length of fluid flow loop 38 (dashed line in FIG. 3) provided by connecting portions 30, 32 and circular portions 26, 28 to the cross-sectional area of the flow path, which in turn provides good sensitivity. While the transformers could be physically brought slightly closer together, to the point that the turns on one core overlap those on the other core and even contact the other core, this is not done, because it would tend to increase the likelihood of a leakage coupling between the transformers.

As is seen in FIG. 5, channel 12 is made of two identical pieces 34, 36, which are solvent bonded together after inserting transformers 14, 16 between them.

Referring to FIG. 6, there is shown the electronic circuitry providing excitation signals to excitation transformer 14 and receiving the signal relating to fluid conductivity from sensing transformer 16. Transformer 14 is connected to receive a 10 KHz square wave excitation signal on the left side of the schematic from oscillator 39 and driver 40. On the right side, sensing transformer 16 is connected to current-to-voltage converter 42, AC amplifier 44, synchronous detector 46, and filter/buffer 48, including, respectively, amplifiers 58, 60, 62, 64 (LF347).

Oscillator 39 includes timer 41 (7555) and flip-flop 42 (74HC74). Both the true and complement outputs of flip-flop 43 are connected to driver interface 45 (75451), the true and complement outputs of which are connected to transformer 14. The true output (Q) of flip-flop 43 is also connected by line 50 to synchronous detector 46.

Excitation transformer 14 is a bifilar wound transformer having 43 turns. Sensing transformer 16 has 89 turns. Both excitation transformer 14 and sensing transformer 16 each also have wrapped around them single wire turns 52, 54, connected to calibration pins 56, for connection to a resistor for use in calibrating the apparatus. The values or numbers of the remaining components on FIG. 6 are as follows:

| Component | Value or Number |
|---|---|
| Capacitors | |
| C8 | 0.0056 |
| C10 | 0.001 |
| C1, C2, C5, C6, C13, C14, C15 | 0.1 |
| C9 | 0.47 |
| C12, C16 | 1.0 |
| C3, C4, C7 | 10.0 |
| C11 | 10.0 pf |
| Resistors | |
| R6 | 13.0 |
| R13 | 100.0 |
| R10 | 0.28K |
| R7, R11 | 2.4K |
| R4 | 10.2K |
| R9, R12 | 14.0K |
| R1, R2 | 23.7K |
| R8 | 28.0K |
| R3 | 49.9K |
| R14 | 100.0K |
| R5 | 274.0K |
| Transistor Q1 | 2N3904 |

Operation

In operation, dialysate flows into inlet 22 through loop 38 and out outlet 24, filling up the entire fluid flow path between inlet 22 and outlet 24 and providing a fluid loop coupled with transformers 14, 16. Because cell 10 is mounted so that the flow paths through connecting portions 30, 32 make a 45° angle with respect to the horizontal, there are no corners at which air bubbles (which would distort measurements) could be trapped; thus, any air bubbles are displaced.

Oscillator 39 provides a 10 KHz square wave applied by driver 40 to excitation transformer 14. A square wave is advantageous because it can be simply generated from inexpensive components providing a constant amplitude, which need not be controlled, as with sinusoidal waves. Driver 40 increases the voltage of the square wave received from oscillator 39 from the 5 volt logic level to 12 volts.

Excitation transformer 14 induces an electrical current in fluid loop 38, which current is then sensed by sensing transformer 16. The current induced in transformer 16 is proportional to the conductivity of liquid in loop 38.

Transformer 16 is capacitively coupled by capacitor C9 to amplifier 58, so that the DC offset is blocked and only the alternating signal is amplified. The output of amplifier 58 is a voltage that is proportional to the conductivity of the liquid in loop 38. Capacitor C12 is used to block the DC offset so that amplifier 60 only amplifies the AC voltage.

Synchronous detector 46 converts the AC voltage from amplifier 44 to a DC voltage output, eliminating extraneous frequencies. When transistor Q1, driven by flip-flop 43, is turned on, it acts as a short to ground, and amplifier 62 operates as an inverting amplifier with a gain of −1; at this time the output of AC amplifier 44 is negative, resulting in a positive output from synchronous detector 46. When transistor Q1 is turned off, it acts as an open circuit, and amplifier 62 has a gain of +1; at this time, the output of AC amplifier 44 is positive, resulting again in a positive output from synchronous detector 46.

The output of synchronous detector 46 charges capacitor C16 through resistor R14. If there are frequencies other than 10 KHz, over a long period the negative and positive components average out; only the signal at the 10 KHz frequency consistently charges capacitor C16, and is passed through amplifier 64 of filter/buffer 48. The output of filter/buffer 48 is a DC voltage proportional to conductivity; it is converted through an A/D converter to a digital signal by a digital processor (both not shown) used to control a dialysate preparation and supply machine of the general type described in U.S. Pat. No. 4,371,385, The circuitry of FIG. 6 can be calibrated by placing a resistor of known value between pins 56, draining the liquid from loop 38 (so that transformers 14, 16 are only coupled through single turns 52, 54) and comparing the output of filter/buffer 48 with the known resistance of the resistor.

Other Embodiments

Other embodiments of the invention are within the scope of the following claims.

What is claimed is:

1. A cell for remotely sensing conductivity of a fluid passing through it, said cell comprising
fluid flow path means for defining a fluid flow path in a supply line, said means having an inlet and an outlet and two fluid paths between said inlet and outlet, thereby defining a fluid loop,
an excitation transformer comprising a first toroidal core having a hole through it and wire turns around it, said core encompassing a portion of said fluid flow path means and said fluid loop therein, and
a sensing transformer comprising a second torodial core having a hole through it and wire turns around it, said core encompassing a portion of said fluid flow path means and said fluid loop therein,
said second toroidal core having a first plane of symmetry that is perpendicular to the axis of its hole, said first plane of symmetry being coplanar with a plane of symmetry of said first toroidal core that is perpendicular to the axis of its hole, to thereby reduce leakage coupling between said transformers,
said fluid flow path means comprising two circular conduit portions having a first length, centers, and ends and two connecting portions connecting the ends of different said circular conduit portions of a second length measured between the centers of said two circular conduit portions, the outer diameter of each said conduit portion being approximately equal to the inner diameter of a said core and said wire turns on it, said first length being approximately equal to the thickness of a said core and said wire turns on it, said second length being approximately equal to the outer diameter of a said core and said wire turns on it.

2. The cell of claim 1 wherein said connecting portions define circular fluid flow passages therein and have flat surfaces that face each other to restrain portions of said toroidal cores between them.

3. The cell of claim 1 wherein said fluid flow path means is made of identical portions, each said portion having a said connecting portion and half of each of said circular conduit portions.

4. The cell of claim 1 wherein there is a first extension in line with one said connecting portion and extending beyond an entrance to one said circular conduit to said inlet, and wherein there is a second extension in line with the other said connecting portion and extending in the other direction beyond an entrance to the other said circular conduit to the outlet, the fluid flow paths in said connecting portions and respective extensions being uninterrupted so as to avoid trapping bubbles when mounted at an inclined angle with respect to the horizontal.

* * * * *